United States Patent
Miyamoto et al.

(10) Patent No.: US 8,362,191 B2
(45) Date of Patent: Jan. 29, 2013

(54) POLYAMIDE RESIN AND HINGED MOLDED PRODUCT

(75) Inventors: Masaaki Miyamoto, Kitakyushu (JP);
Tatsuya Hitomi, Kitakyushu (JP);
Yuuichi Nishida, Kitakyushu (JP)

(73) Assignee: Mitsubishi Chemical Corporation, Tokyo (JP)

( * ) Notice: Subject to any disclaimer, the term of this patent is extended or adjusted under 35 U.S.C. 154(b) by 180 days.

(21) Appl. No.: 12/662,600

(22) Filed: Apr. 26, 2010

(65) Prior Publication Data

US 2010/0206459 A1     Aug. 19, 2010

Related U.S. Application Data

(60) Division of application No. 12/461,446, filed on Aug. 12, 2009, now abandoned, which is a continuation of application No. 11/596,619, filed on Mar. 9, 2007, now abandoned.

(30) Foreign Application Priority Data

May 21, 2004  (JP) ................. 2004-152059

(51) Int. Cl.
*C08G 69/02*  (2006.01)
*C08G 69/26*  (2006.01)
*C08L 77/04*  (2006.01)
*C08L 77/06*  (2006.01)
*C08L 79/02*  (2006.01)

(52) U.S. Cl. ........ 528/310; 524/606; 524/607; 528/335; 528/338; 525/66; 525/92

(58) Field of Classification Search .................. 524/607; 525/66, 92; 528/338
See application file for complete search history.

(56) References Cited

U.S. PATENT DOCUMENTS 2,130,948 A     9/1938  Hume
5,853,831 A *  12/1998  Urabe et al. ................. 428/35.7

FOREIGN PATENT DOCUMENTS

| JP | 61/229540 A | 10/1986 |
| JP | 61-229540 A | 10/1986 |
| JP | 07-082474 | 3/1995 |
| JP | 09/124934 | 5/1997 |
| JP | 09-249808 | 9/1997 |
| JP | 2000-204243 | 7/2000 |
| JP | 2000-351897 A | 12/2000 |
| JP | 2003-292612 | 10/2003 |
| JP | 2003-292612 A | 10/2003 |
| JP | 2003292612 A * | 10/2003 |
| JP | 2004-269634 | 9/2004 |
| JP | 2004-269634 A | 9/2004 |
| WO | 93/00385 A1 | 1/1993 |
| WO | WO 93/00385 | 1/1993 |
| WO | WO 9300385 A1 * | 1/1993 |

OTHER PUBLICATIONS

Machine Translation of JP 2003-292612.*
Notification of Reasons for Refusal in JP 2005/145,847, May 13, 2010.

(Continued)

*Primary Examiner* — Ling Choi
*Assistant Examiner* — Darcy D Laclair Lynx
(74) *Attorney, Agent, or Firm* — Nixon & Vanderhye P.C.

(57) ABSTRACT

A polyamide resin comprising a dicarboxylic acid constitutional unit comprising an adipic acid unit and a diamine constitutional unit comprising a pentamethylenediamine unit and a hexamethylenediamine unit wherein a weight ratio of the pentamethylenediamine unit to the hexamethylenediamine unit being in the range of 95:5 to 60:40; a vibration-welded molded product having an excellent vibration welding strength, a hinged molded product and a binding band having an excellent low-temperature toughness, and a filament having an excellent transparency which are obtained from the polyamide resin; and a hinged molded product comprising a polyamide resin constituted of an adipic acid unit and a pentamethylenediamine unit.

5 Claims, 4 Drawing Sheets

OTHER PUBLICATIONS

Office Action with English translation in CN application No. 200910171005.X issued Apr. 20, 2011.
English translation of Chinese Office Action issued Jun. 2, 2011 in CN 200910171004.5.1.
International Search Report of PCT/JP2005/009144, mailed Aug. 2, 2005.
Supplementary Search Report mailed Jan. 22, 2009 in the counterpart European application SN 0574158.
Chinese Official Action in Chinese application 200580015837.2 and English translation.
Official Action (English translation) in Chinese counterpart application 2005800158372.
Office Action in EP 05741581.2 issued Jul. 1, 2011.
Machine translation of JP 2004-75932; Mar. 11, 2004 publication date.

* cited by examiner (a)

(b)

(a)

(b)

POLYAMIDE RESIN AND HINGED MOLDED PRODUCT

This application is a divisional of application Ser. No. 12/461,446 filed Aug. 12, 2009 now abandoned, which in turn is a continuation of application Ser. No. 11/596,619 filed Mar. 9, 2007 now abandoned, which in turn claims priority of application Ser. No. PCT/JP2005/009144, filed 19 May 2005, which designated the U.S. and claims priority of JP 2004-152059, filed 21 May 2004, the entire contents of each of which are hereby incorporated by reference.

TECHNICAL FIELD

The present invention relates to a polyamide resin, and more particularly to a polyamide resin comprising an adipic acid unit, a pentamethylenediamine unit and a hexamethylenediamine unit as constitutional components thereof which can be produced by using raw materials that are free from generation of carbon dioxide ($CO_2$) causing global warming problems; and a vibration-welded molded product having an excellent vibration welding strength, a hinged molded product and a binding band having an excellent low-temperature toughness, and a filament having an excellent transparency which are produced from the polyamide resin. Further, the present invention relates to a hinged molded product, and more particularly to a hinged molded product obtained from a polyamide resin that is more excellent in hinge property and heat resistance (melting point) than those of 6-nylon, and simultaneously has a good rigidity (bending modulus) equal to or higher than that of 6-nylon.

BACKGROUND ARTS 6-nylon and 66-nylon are resins having excellent moldability, heat resistance, chemical resistance and mechanical properties and, therefore, have been extensively used in various applications such as automobile and vehicle-related parts, electric and electronic parts, household or business electric equipment-related parts, computer-related parts, facsimile or copier-related parts, mechanical parts, packaging materials and fishing materials. In particular, in the application field of automobile and vehicle-related parts, intensive studies have been made to apply these nylons to under-hood parts for automobiles such as intake manifold, hinged clip (hinged molded product), binding band, resonator, air cleaner, engine cover, rocker cover, cylinder head cover, timing belt cover, gasoline tank, gasoline sub-tank, radiator tank, inter-cooler tank, oil reservoir tank, oil pan, electric power steering gear, oil strainer, canister, engine mount, junction block, relay block, connector, corrugated tube and protector.

These under-hood parts for automobiles have been required to have a higher strength in order to meet various requirements owing to a complicated structure of the parts and a reduced thickness thereof for the purpose of weight reduction. Among these under-hood parts for automobiles, the intake manifold having a larger size is more susceptible to a weight-reduction effect than the other automobile parts by decreasing a thickness thereof. However, the intake manifold must be kept safe without damage thereto even when an internal pressure thereof is increased owing to backfire of an engine, etc. Therefore, at the present time, reduction in thickness of these parts such as the intake manifold is possible only to a limited extent.

In recent years, as the material for resin intake manifolds, there has been mainly used glass fiber-reinforced 6-nylon, and the intake manifolds have been mainly produced therefrom by a vibration-welding method. Also, there has been proposed the resin intake manifold produced by using 56-nylon instead of the 6-nylon (for example, refer to Patent document 1). However, the 56-nylon tends to be insufficient in vibration-welding strength, and further deteriorated in retention heat stability, and, therefore, is unsuitable for large-size molded products requiring a long molding cycle time such as intake manifolds. For this reason, it has been demanded to provide polyamide resins having more excellent vibration-welding strength and retention heat stability than those of 56-nylon.

There is also known a 56/66 nylon containing a smaller amount of 56-nylon and a larger amount of 66-nylon (ratio 56/66=0.5/99.5 to 40/60 mol % and preferably 0.5/99.5 to 10/90 mol %) (for example, refer to Patent document 2). Since the polyamide resin of this type aims at suppressing gelation of 66-nylon while maintaining functions of 66-nylon, the amount of 56-nylon added thereto is small. Therefore, it is considered that the polyamide resin exhibits only a vibration-welding strength substantially identical to that of 66-nylon, though it is not clearly known. Thus, in order to apply the polyamide resin to production of large-size thin-walled molded products, further improvement in properties thereof are required.

Hinged molded products have been frequently used for under-hood parts for automobiles. At the present time, the hinged molded products requiring a high heat resistance have been produced from 66-nylon, whereas the hinged molded products requiring a high toughness have been produced from 6-nylon. The 66-nylon has a melting point as high as 264° C. and a high crystallinity and, therefore, is slightly low in toughness. Therefore, the hinged molded products produced from the 66-nylon tend to suffer from breakage upon bending. On the other hand, the 6-nylon has a lower crystallinity than that of the 66-nylon and, therefore, exhibits a good toughness. However, the melting point of the 6-nylon is 224° C., i.e., much lower by 40° than that of the 66-nylon.

With the recent increasing tendency that hinged parts have a complicated shape, it has been demanded to provide polyamide resins having a more excellent hinge property than that of 6-nylon. Further, with the reduction or compactness in size of an engine room of automobiles, it has been demanded to provide polyamide resins having a higher heat resistance (melting point). In addition, these polyamide resins are required to have a rigidity (bending modulus) identical to or higher than that of 6-nylon.

As the method of improving a hinge property of hinged molded products, there is known the method of blending the polyamide resin with a boron nitride powder and an aliphatic carboxylic acid derivative (for example, refer to Patent document 3). However, it is considered that the resin composition of this type fails to exhibit an improved heat resistance (melting point).

Also, there is known the method of blending the polyamide resin with a polyolefin such as polypropylene and polyethylene (for example, refer to Patent document 4 However, the polyamide resin composition of this type tends to be deteriorated in heat resistance (melting point) or mechanical properties such as bending modulus as compared to those of the polyamide resin.

As the polyamide resin satisfying both the above hinge property and the heat resistance (heat-deforming temperature), there is known the polyamide resin composition composing an aromatic polyamide resin, a modified polyolefin, and an epoxy-containing polymer or an epoxidated diene-based block copolymer (for example, refer to Patent documents 5 and 6). However, the bending modulus of the polyamide resin composition of this type is as low as about 1500 to 1900 MPa which is considerably deteriorated as compared to a bending modulus of ordinary 6-nylon (about 2550 MPa) and that of ordinary 66-nylon (about 2940 MPa). Therefore, the polyamide resin composition tends to be deficient in rigidity as an important mechanical property. For this reason, it has been demanded to provide polyamide resins capable of exhibiting more excellent hinge property and heat resistance (melting point) than those of 6-nylon and simultaneously having a rigidity (bending modulus) identical to or higher than that of 6-nylon.

Also, as the raw material of the polyamide resin, there are used so-called fossil materials such as naphtha. However, with the recent requirements for prevention of global warming by suppressing discharge of carbon dioxide as well as establishment of recycling type society, it has been demanded to replace the material for production of the polyamide resins with a biomass-derived raw material. More specifically, it has been required that the polyamide is produced from such a raw material having a high biomass ratio (ratio of the biomass-derived material to the whole raw materials used for production of the polyamide resin).

The use of the biomass-derived material has been extensively demanded in various application fields including not only automobiles, but also electric and electronic parts, films and filaments. Specific examples of these parts include vibration-welded molded products such as the above intake manifold having an excellent vibration welding strength, hinged molded products and binding bands having an excellent low-temperature toughness, and filaments having an excellent transparency.

Known polyamide resins produced by polymerizing the biomass-derived material include, for example, 56 nylon. The 56 nylon has substantially the same heat resistance and mechanical properties as those of 6 nylon or 66 nylon. As the method for production of the 56 nylon, there are known the method of heat-polycondensing diaminopentane with adipic acid (for example, refer to Patent document 7), and the method of preparing a salt of diaminopentane and adipic acid and then heat-polycondensing the salt (for example, refer to Patent document 8). However, as described above, the 56 nylon tends to be deteriorated in vibration-welding strength and retention heat stability. For this reason, it has been demanded to develop polyamide resins which can be produced by polymerizing a biomass-derived raw material, and are capable of providing binding bands having an excellent low-temperature toughness and filaments having an excellent transparency. However, there are conventionally unknown hinged molded products produced from the 56 nylon.

Patent Document 1: Japanese Patent Application Laid-open (KOKAI) No. 2004-269634
Patent Document 2: PCT Pamphlet No. 93/00385
Patent Document 3: Japanese Patent Application Laid-open (KOKAI) No. 7-82474.
Patent Document 4: Japanese Patent Application Laid-open (KOKAI) No. 9-249808.
Patent Document 5: Japanese Patent Application Laid-open (KOKAI) No. 9-124934
Patent Document 6: Japanese Patent Application Laid-open (KOKAI) No. 2000-204243
Patent Document 7: Japanese Patent Application Laid-open (KOKAI) No. 2003-292612
Patent Document 8: U.S. Pat. No. 2,130,948

DISCLOSURE OF THE INVENTION

Problem to be Solved by the Invention

Thus, the present invention has been made in view of the above conventional problems, and an object of the present invention is to provide a polyamide resin which is excellent in vibration-welding strength, retention heat stability, low-temperature toughness and transparency, and can be produced from a biomass-derived material.

Another object of the present invention is to provide a polyamide resin composition containing the above polyamide resin.

A further object of the present invention is to provide a vibration-welded molded product, a hinged molded product, a binding band and a filament which comprise the above polyamide resin or polyamide resin composition.

The other object of the present invention is to provide a hinged molded product produced from a polyamide resin which is more excellent in hinge property and heat resistance (melting point) than those of 6-nylon and simultaneously exhibit a good rigidity (bending modulus) identical to or higher than that of 6-nylon.

Means for Solving the Problem

As a result of the present inventors' earnest study for solving the above problems, it has been found that the above objects can be attained by such a polyamide resin constituted of an adipic acid unit, a pentamethylenediamine unit and a hexamethylenediamine unit in which a ratio between contents of the pentamethylenediamine unit and the hexamethylenediamine unit lies within a specific range, and that a hinged molded product containing a polyamide resin constituted of an adipic acid unit and a pentamethylenediamine unit can simultaneously satisfy a good hinge property, a high heat resistance (melting point) and a good rigidity (bending modulus). The present invention has been attained on the basis of the above findings.

That is, in a first aspect of the present invention, there is provided a polyamide resin comprising a dicarboxylic acid constitutional unit comprising an adipic acid unit and a diamine constitutional unit comprising a pentamethylenediamine unit and a hexamethylenediamine unit, a weight ratio of the pentamethylenediamine unit to the hexamethylenediamine unit being in the range of 95:5 to 5:95, and the pentamethylenediamine unit being formed from pentamethylenediamine which is produced from lysine using a lysine decarboxylase, cells capable of producing the lysine decarboxylase or a treated product of the cells.

In a second aspect of the present invention, there is provided a polyamide resin comprising a dicarboxylic acid constitutional unit comprising an adipic acid unit and a diamine constitutional unit comprising a pentamethylenediamine unit and a hexamethylenediamine unit, a weight ratio of the pentamethylenediamine unit to the hexamethylenediamine unit being in the range of 95:5 to 60:40.

In a third aspect of the present invention, there is provided a polyamide resin composition comprising the above polyamide resin and an inorganic filler, a content of the inorganic filler being 0.01 to 150 parts by weight on the basis of 100 parts by weight of the polyamide resin.

In a fourth aspect of the present invention, there is provided a vibration-welded molded product comprising the above polyamide resin or the above polyamide resin composition.

In a fifth aspect of the present invention, there is provided a hinged molded product comprising the above polyamide resin or the above polyamide resin composition.

In a sixth aspect of the present invention, there is provided a binding band comprising the above polyamide resin or the above polyamide resin composition.

In a seventh aspect of the present invention, there is provided a filament comprising the above polyamide resin or the above polyamide resin composition.

In a eighth aspect of the present invention, there is provided a hinged molded product comprising a polyamide resin constituted of an adipic acid unit and a pentamethylenediamine unit.

Effect of the Invention

The polyamide resin or polyamide resin composition of the present invention is excellent in vibration-welding strength, retention heat stability, low-temperature toughness and transparency. Also, the polyamide resin or polyamide resin composition of the present invention can provide a vibration welded molded product, a hinged molded product, a binding band and a filament. In particular, the hinged molded product produced from the polyamide resin of the present invention can exhibit an extremely high hinge property. Further, the polyamide resin of the present invention can be produced from a biomass-derived material, and is thus expected to exhibit a remarkably high effect of reducing a burden to environments in various industrial fields. Therefore, the present invention has a high industrial value in this regard. In addition, the hinged molded product of the present invention can exhibit an extremely high hinge property, and have a higher heat resistance (melting point) than that of a hinged molded product produced from 6 nylon as well as mechanical properties identical to or higher than those of the hinged molded product produced from 6 nylon. For this reason, the hinged molded product is suitable, in particular, as, hinged parts used in an engine room of automobiles, and may also be useful as various hinged parts. Further, the polyamide resin and the hinged molded product of the present invention can be produced from a biomass-derived material, and is thus expected to exhibit a remarkably high effect of reducing a burden to environments in various industrial fields. Therefore, the present invention also has a high industrial value in this regard.

BRIEF DESCRIPTION OF THE DRAWINGS

FIG. 3 is a side view showing a welded side of respective hollow parts as primary molded products used in a vibration welding test in Examples according to the present invention in which FIG. 3(a) is a view showing the hollow part having a convex portion as a welding margin in its portion to be welded; and FIG. 3(b) is a view showing the hollow part having a flat portion to be welded.

EXPLANATION OF REFERENCE NUMERALS

Figure 1:
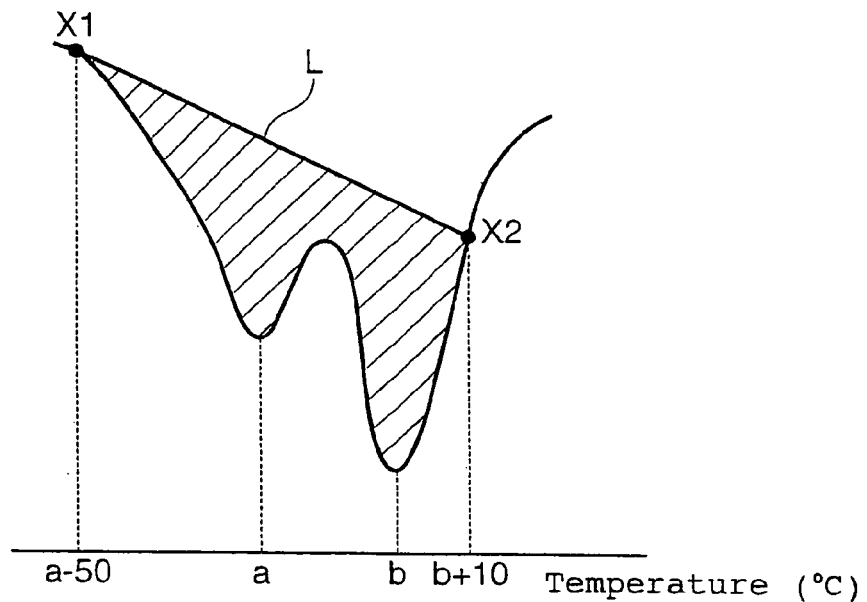
FIG. 1 is an explanatory view for determining an endothermic peak area.

1: Upper opening portion
1': Upper opening portion
2: Lower opening portion

PREFERRED EMBODIMENTS OF THE INVENTION

The present invention is described in detail below. Although typical examples of preferred embodiments of the present invention are explained hereinlater, these examples are only illustrative and not intended to limit the scope of the present invention. First, the polyamide resins according to the first and second aspects of the present invention are described. The polyamide resins according to the first and second aspects of the present invention are respectively constituted of a dicarboxylic acid constitutional unit comprising an adipic acid unit and a diamine constitutional unit comprising a pentamethylenediamine unit and a hexamethylenediamine unit.

The content of the adipic acid unit in the dicarboxylic acid constitutional unit of the polyamide resin is usually not less than 90% by weight and preferably not less than 95% by weight. The dicarboxylic acid constitutional unit may be composed of the adipic acid unit only. The total content of the pentamethylenediamine unit and the hexamethylenediamine unit in the diamine constitutional unit of the polyamide resin is usually not less than 90% by weight and preferably not less than 95% by weight. The diamine constitutional unit may be composed of the pentamethylenediamine unit and the hexamethylenediamine unit only.

In the polyamide resin according to the first aspect of the present invention, the weight ratio of the pentamethylenediamine unit to the hexamethylenediamine unit in the diamine constitutional unit is 95:5 to 5:95, preferably 95:5 to 60:40 and more preferably 90:10 to 70:30. In the polyamide resin according to the second aspect of the present invention, the weight ratio of the pentamethylenediamine unit to the hexamethylenediamine unit in the diamine constitutional unit is 95:5 to 60:40, preferably 92.5:7.5 to 65:35 and more preferably 90:10 to 70:30. When the weight ratio of the pentamethylenediamine unit to the hexamethylenediamine unit is more than 95%, the resultant polyamide resin tends to be deteriorated in vibration-welding strength, retention heat stability and transparency of the filament produced therefrom. On the other hand, When the weight ratio of the pentamethylenediamine unit to the hexamethylenediamine unit is less than the above-specified range, the resultant polyamide resin tends to be deteriorated in vibration-welding strength, retention heat stability, low-temperature toughness, transparency of the filament produced therefrom and biomass ratio. Meanwhile, the weight ratio of the pentamethylenediamine unit to the hexamethylenediamine unit in the diamine constitutional unit of the polyamide resin may be determined, for example, by the following method. That is, the polyamide resin is hydrolyzed with an acid or an alkali to decompose the resin into pentamethylenediamine, hexamethylenediamine and adipic acid as constitutional units thereof, and contents of the respective components are determined by a liquid chromatography, etc., using a calibration curve previously prepared.

The polyamide resin of the present invention may be in the form of either a blended mixture of homopolyamides or a copolymer as long as these polymers contain the above constitutional units. More specifically, the polyamide may be in the form of a blended mixture of a polyamide 56 homopolymer and a polyamide 66 homopolymer or a copolyamide comprising pentamethylenediamine, hexamethylenediamine and adipic acid as constitutional units thereof. Among them, the copolyamide is especially preferred in order to achieve the aimed effects of the present invention.

The polyamide resin of the present invention may also contain comonomer components other than pentamethylenediamine, hexamethylenediamine and adipic acid as essential constitutional units thereof in an amount of usually less than 10% by weight and preferably less than 5% by weight unless the addition thereof adversely affects the aimed effects of the present invention. Examples of the comonomer components may include amino acids such as 6-aminocaproic acid, 11-aminoundecanoic acid, 12-aminododecanoic acid and p-aminomethylbenzoic acid, and lactams such as ε-caprolactam and ω-laurolactam.

Examples of the dicarboxylic acid as the comonomer component may include aliphatic dicarboxylic acids such as oxalic acid, malonic acid, succinic acid, glutaric acid, adipic acid, pimelic acid, suberic acid, azelaic acid, sebacic acid, undecanedioic acid, dodecanedioic acid, brassilic acid, tetradecanedioic acid, pentadecanedioic acid and octadecanedioic acid, alicyclic dicarboxylic acids such as cyclohexanedicarboxylic acid, and aromatic dicarboxylic acids such as phthalic acid, isophthalic acid, terephthalic acid and naphthalenedicarboxylic acid.

Examples of the diamine as the comonomer component may include aliphatic diamines such as ethylenediamine, 1,3-diaminopropane, 1,4-diaminobutane, 1,7-diaminoheptane, 1,8-diaminooctane, 1,9-diaminononane, 1,10-diaminodecane, 1,11-diaminoundecane, 1,12-diaminododecane, 1,13-diaminotridecane, 1,14-diaminotetradecane, 1,15-diaminopentadecane, 1,16-diaminohexadecane, 1,17-diaminoheptadecane, 1,18-diaminooctadecane, 1,19-diaminononadecane, 1,20-diaminoeicosane and 2-methyl-1,5-diaminopentane; alicyclic diamines such as cyclohexane diamine and bis-(4-aminohexyl)methane; and aromatic diamines such as xylenediamine.

The polymerization degree of the polyamide resin of the present invention is not particularly limited. A 98 wt % sulfuric acid solution of the polyamide resin (concentration of the polyamide resin: 0.01 g/mL) has a relative viscosity of usually 1.5 to 8.0 and preferably 1.8 to 5.0 as measured at 25° C. When the relative viscosity of the solution is less than 1.5, the polyamide resin tends to be insufficient in strength upon actual use. When the relative viscosity of the solution is more than 8.0, the polyamide resin tends to be deteriorated in fluidity and exhibit a poor moldability.

When the polyamide resin of the present invention is subjected to DSC measurement, the ratio of an endothermic peak area of the polyamide resin as measured at a temperature of not lower than 240° C. to a whole endothermic peak area thereof is usually not more than 60% and preferably not more than 50%. When the ratio of the endothermic peak area of the polyamide resin as measured at a temperature of not lower than 240° C. to a whole endothermic peak area thereof is more than 60%, the polyamide resin tends to be deteriorated in a vibration-welding strength, retention heat stability and low-temperature toughness. The DSC measurement may be conducted using "Robot DSC" manufactured by Seiko Denshi Kogyo Co., Ltd. In the specific procedure for the DSC measurement, about 5 mg of the obtained polyamide resin is placed in a sample pan, heated to 290° C. under a nitrogen atmosphere, and then held at 290° C. for 3 min. Thereafter, the polyamide resin is cooled to 30° C. at a temperature drop rate of 20° C./min and successively held at 30° C. for 3 min, and then heated again from 30° C. to 290° C. at a temperature rise rate of 20° C./min to observe and measure an endothermic peak thereof. An endothermic peak area of the polyamide resin is determined from the thus prepared endothermic peak curve.

Figure 2:
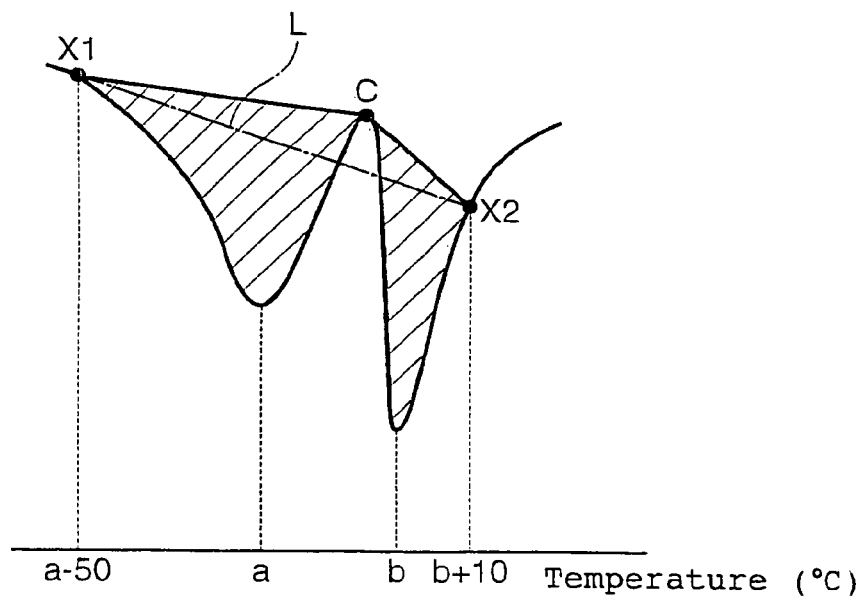
FIG. 2 is an explanatory view for determining an endothermic peak area.

The method of determining the endothermic peak area of the polyamide resin is explained by referring to FIGS. 1 and 2. In endothermic peaks observed in the range between 200° C. and 290° C., when the temperature of an endothermic peak observed as a minimum temperature is expressed by a (° C.) and the temperature of an endothermic peak observed as a maximum temperature is expressed by b (° C.), and endothermic points observed at temperatures (a−50(° C.)) and (b+10(° C.)) are expressed by X1 and X2, respectively, the endothermic peak area is defined by such an area surrounded by a line (L) connecting the endothermic points X1 and X2 and the endothermic peak curve (refer to the hatched portion in FIG. 1). Meanwhile, as shown in FIG. 2, if the line (L) connecting the endothermic points X1 and X2 (indicated by a dashed line in FIG. 2) is intersected with the endothermic peak curve between the endothermic points X1 and X2, the endothermic peak area is defined by an area surrounded by the endothermic peak curve and a bending line (X1-C-X2) wherein C is a point at which the endotherm becomes minimum between the endothermic peaks (i.e., the hatched portion shown in FIG. 2).

The melting point (Tm) of the polyamide resin of the present invention as observed on a high-temperature side is usually 225 to 255° C. and preferably 230 to 253° C. Meanwhile, the melting point is determined as the endothermic peak temperature observed in the DSC measurement. When two or more endothermic peaks are detected, the polyamide resin has a plurality of melting points corresponding to the endothermic peaks.

The polyamide resin of the present invention may be blended with other components at an optional stage from production (polycondensation) of the polyamide resin to molding thereof unless the addition thereof adversely affects the aimed effects of the present invention. Examples of the other components blended in the polyamide resin may include antioxidants and/or heat stabilizers, weather-resisting agents, nucleating agents, mold release agents and/or lubricants, pigments, dyes, plasticizers, antistatic agents, flame retardants and other polymers.

Specific examples of the antioxidants and/or heat stabilizers may include hindered phenol-based compounds, hydroquinone-based compounds, phosphite-based compounds and substituted compounds thereof, copper halides and iodine compounds. Specific examples of the weather-resisting agents may include resorcinol-based compounds, salicylate-based compounds, benzotriazole-based compounds, benzophenone-based compounds and hindered amine-based compounds. Specific examples of the nucleating agents may include inorganic fine particles such as talc, kaolin, silica and boron nitride, metal oxides and high-melting nylons. Specific examples of the mold release agents and/or lubricants may include aliphatic alcohols, aliphatic amides, aliphatic bisamides, bisureas and polyethylene waxes. Specific examples of the pigments may include cadmium sulfide, phthalocyanine and carbon black. Specific examples of the dyes may include nigrosine and aniline black. Specific examples of the plasticizers may include octyl p-oxybenzoate and N-butyl benzenesulfonamide.

Specific examples of the antistatic agents may include alkyl sulfate-type anionic antistatic agents, quaternary ammonium salt-type cationic antistatic agents, nonionic antistatic agents such as polyoxyethylene sorbitan monostearate, and betaine-based amphoteric antistatic agents. Specific examples of the flame retardants may include melamine cyanurate, hydroxides such as magnesium hydroxide and aluminum hydroxide, ammonium polyphosphates, brominated polystyrenes, brominated polyphenylene oxides, brominated polycarbonates, brominated epoxy resins, and combination of these bromine-based compounds with antimony trioxide. Specific examples of the other polymers may include other polyamides, polyethylene, polypropylene, polyesters, polycarbonates, polyphenylene ethers, polyphenylene sulfides, liquid crystal polymers, polysulfones, polyether sulfones, ABS resins, SAN resins and polystyrenes.

Among these components, when the polyamide resin is used for injection molding and non-reinforcing purposes for hinged molded products, binding bands, etc., the nucleating agents or mold release agents are preferably dry-blended in the polyamide resin in order to enhance a moldability thereof unless the addition thereof adversely affects the aimed effects of the present invention.

The polyamide resin of the present invention (including homopolyamide and polyamide copolymer) may be produced by known methods. Specific methods for producing the polyamide resin are described in "Handbook for Polyamide Resins" edited by FUKUMOTO, Osamu (published by Nikkan Kogyo Newspaper Co., Ltd.), etc. The polyamide 56 copolymer is preferably produced by the method of polycondensing an aliphatic diamine component comprising pentamethylenediamine and hexamethylenediamine in a total amount of usually not less than 90% and preferably not less than 95% with a dicarboxylic acid component comprising adipic acid in an amount of usually not less than 90% and preferably not less than 95%. More specifically, in the preferred production method, a salt of pentamethylenediamine and adipic acid and a salt of hexamethylenediamine and adipic acid are prepared, and mixed with each other under the coexistence of water, and then the resultant mixture is heated to allow a dehydration reaction (heat-polycondensation) thereof to proceed. In this case, by varying a mixing ratio between the salt of pentamethylenediamine and adipic acid and the salt of hexamethylenediamine and adipic acid, it is possible to obtain polyamide resins having different copolymerization compositions from each other. The mixing ratio between the salt of pentamethylenediamine and adipic acid and the salt of hexamethylenediamine and adipic acid is preferably controlled such that the molar ratio of the aliphatic diamine to the dicarboxylic acid is usually in the range of 1.00:1 to 1.05:1.

Meanwhile, in the present invention, the heat polycondensation means a process for production of polyamide resins in which a maximum temperature of the polymerization reaction mixture reaches 200° C. or higher. The upper limit of the maximum temperature is usually not more than 300° C. in the consideration of a heat stability of the polyamide resin upon the polymerization reaction. The polymerization reaction may be conducted by either a batch method or a continuous method.

The polyamide resin produced by the above method may be further subjected to solid phase polymerization after the heat polycondensation, thereby enhancing a molecular weight of the obtained polyamide resin. The solid phase polymerization may be conducted, for example, by heating the polyamide resin at a temperature of not lower than 100° C. and not higher than a melting point thereof in vacuum or under an inert gas atmosphere.

In the polyamide resin described in the first aspect of the present invention, pentamethylenediamine as the raw component may be produced from lysine using a lysine decarboxylase, cells capable of producing the lysine decarboxylase or a treated product of the cells. In the polyamide resin described in the second aspect of the present invention, pentamethylenediamine as the raw component is also preferably produced from lysine using a lysine decarboxylase, cells capable of producing the lysine decarboxylase or a treated product of the cells. The use of such a pentamethylenediamine produced from lysine enables the resultant polyamide resin to exhibit a high biomass ratio (ratio of a biomass-derived raw material to whole raw materials used for production of the polyamide resin). The biomass ratio (ratio of a biomass-derived raw material to whole raw materials used for production of the polyamide resin) in the polyamide resin of the present invention is preferably not less than 5%. When the biomass ratio in the polyamide resin is less than 5%, it is not possible to attain the effect of suppressing generation of carbon dioxide causing the global warming problem.

More specifically, the above pentamethylenediamine may be produced, for example, by the following method. That is, a lysine-containing solution is subjected to enzymatic decarboxylation reaction while adding an acid to the lysine-containing solution so as to keep a pH value of the solution suitable for the enzymatic decarboxylation reaction. Examples of the acid used in the enzymatic decarboxylation reaction may include inorganic acids such as hydrochloric acid, sulfuric acid and phosphoric acid, and organic acids such as acetic acid. The obtained reaction product solution may be subjected to ordinary separation and purification methods to recover liberated pentamethylenediamine therefrom. When a dicarboxylic acid such as adipic acid is used as the acid added upon the enzymatic decarboxylation reaction, it is also possible to recover a pentamethylenediamine dicarboxylate which may be directly used as the raw material for production of the polyamide. The method of producing pentamethylenediamine adipate by enzymatic decarboxylation reaction of lysine using adipic acid as the above acid is described in Japanese Patent Application Laid-open (KOKAI) No. 2005-6650.

Next, the polyamide resin composition according to the third aspect of the present invention is explained. The polyamide resin composition of the present invention comprises the polyamide resin according to the first or second aspect of the present invention, and an inorganic filler.

Examples of the inorganic filler may include graphite, barium sulfate, magnesium sulfate, calcium carbonate, magnesium carbonate, antimony oxide, titanium oxide, aluminum oxide, zinc oxide, iron oxide, zinc sulfide, zinc, lead, nickel, aluminum, copper, iron, stainless steel, glass fiber, glass flakes, glass beads, carbon fiber, talc, silica, kaolin, clay, wollastonite, mica, boron nitride, potassium titanate, aluminum borate, bentonite, montmorillonite, synthetic mica, etc. Among these inorganic fillers, glass fiber is preferred because of a high reinforcing effect and relatively low costs thereof.

As the glass fiber, there may be used those glass fibers ordinarily used for thermoplastic resins. Among these glass fibers, preferred are chopped strands produced from E-glass (alkali-free glass). The fiber diameter of the glass fiber is usually 1 to 20 μm and preferably 5 to 15 μm. The glass fiber is preferably surface-treated with a silane coupling agent, etc., in order to enhance adhesion to the polyamide resin.

The inorganic filler may be blended in the polyamide resin at an optional stage from production (polycondensation) of the polyamide resin to molding thereof. The inorganic filler is preferably charged into an extruder which is in the course of molding the polyamide resin, and melt-kneaded with the polyamide resin therein.

The amount of the inorganic filler blended is 0.01 to 150 parts by weight and preferably 0.01 to 100 parts by weight based on 100 parts by weight of the polyamide resin. When the amount of the inorganic filler blended is more than 150 parts by weight, the resultant composition tends to be deteriorated in fluidity.

The polyamide resin composition of the present invention may also be blended with other components at an optional stage from production (polycondensation) of the polyamide resin to molding thereof unless the addition thereof adversely affects the effects of the present invention. Examples of the other components may include those described in the first and second aspects of the present invention, namely, antioxidants and/or heat stabilizers, weather-resisting agents, nucleating agents, mold release agents and/or lubricants, pigments, dyes, plasticizers, antistatic agents, flame retardants and other polymers.

Next, the vibration-welded molded product according to the fourth aspect of the present invention, the hinged molded product according to the fifth aspect of the present invention, the binding band according to the sixth aspect of the present invention and the filament according to the seventh aspect of the present invention are explained below. The vibration-welded molded product, hinged molded product, binding band and filament of the present invention respectively comprise the polyamide resin according to the first or second aspect of the present invention or the polyamide resin composition according to the third aspect of the present invention.

The vibration-welded molded product of the present invention may be produced by the following method. First, a plurality of parts are respectively molded from the polyamide resin or the polyamide resin composition to form primary molded products. The method of forming the primary molded products is not particularly limited, and there may be used any optional molding methods such as an injection-molding method, a film-forming method, a melt-sinning method, a blow-molding method and a vacuum forming method. Among these molding methods, preferred is the injection-molding method. The shape of the primary molded product is not particularly limited, and the primary molded product may be of any desired shape. Also, the shapes of a plurality of the primary molded products may be identical to or different from each other.

Next, a plurality of the thus molded parts as primary molded products are bonded together by vibration welding to obtain a vibration-welded molded product. In the vibration welding method, a frequency of vibration used therefor is usually 100 to 300 Hz, and an amplitude thereof is usually 0.5 to 2.0 mm and preferably 0.8 to 1.6 mm. The welding pressure used in the vibration welding is usually 0.5 to 10 MPa and preferably 0.8 to 6 MPa. When the welding pressure is too high or too low, the resultant vibration-welded molded product tends to be deteriorated in welding strength. In particular, when the welding pressure is too low, welded portions of the obtained vibration-welded molded product tend to be insufficient in welding strength, resulting in poor air tightness in the case where the molded product is a hollow product. The welding time used under a given pressure may be controlled so as to obtain the aimed welding margin, and a retention time of the molded product after stopping application of the vibration may be controlled so as to allow the welded portions to be fully solidified.

The hinged molded product and binding band of the present invention may be obtained by molding the polyamide resin or the polyamide resin composition of the present invention into a desired shape by any optional methods similarly to those used for production of the primary molded product of the vibration-welded molded product. Among the molding methods, especially preferred is an injection-molding method.

Specific examples of the hinged molded product and the binding band may include hinged clips, hinged connectors, hinged binding bands, etc. The thickness of the hinged portion of these products is usually 0.2 to 0.8 mm and preferably 0.3 to 0.6 mm. When the thickness of the hinged portion is less than 0.2 mm, the polyamide resin used in the hinged portion tends to be deteriorated in fluidity. On the other hand, when the thickness of the hinged portion is more than 0.8 mm, the crystallinity of the polyamide used in the hinged portion tends to be increased, so that the hinged portion tends to suffer from breakage or cracks upon bending.

The filament of the present invention may be produced by forming the polyamide resin or the polyamide resin composition of the present invention into a filament shape by a melt-spinning method. The filament of the present invention is preferably applied to a pile-containing portion of respective constituting layers (including a base fabric, a pile layer and a packing layer) of a mat. In particular, when applying the filament to such a mat requiring a good anti-fouling property, the filament of the present invention is preferably blended with a nucleating agent such as talc, silica, kaolin and clay. The filament of the present invention may also be applied to not only the constituting layers of the mat, but also carpets for domestic use, carpets for offices, carpets for automobiles, raw threads for clothing, etc.

As described above, the polyamide resin and the polyamide resin composition of the present invention may be formed into a desired shape by an optional molding method such as an injection-molding method, a film-forming method, a melt-spinning method, a blow-molding method and a vacuum forming method. For example, the polyamide resin and the polyamide resin composition of the present invention may be used in injection-molded products, films, sheets, filaments, tapered filaments, fibers, etc., as well as adhesives and paints.

Specific examples of the applications of the polyamide resin and the polyamide resin composition of the present invention may include automobile and vehicle-related parts, e.g., automobile under-hood parts such as intake manifold, hinged clips (hinged molded products), binding bands, resonators, air cleaners, engine covers, rocker covers, cylinder head covers, timing belt covers, gasoline tanks, gasoline sub-tanks, radiator tanks, intercooler tanks, oil reservoir tanks, oil pans, electric gears, oil strainers, canisters, engine mounts, junction blocks, relay blocks, connectors, corrugated tubes and protectors, automobile exterior parts such as door handles, fenders, hood bulges, roof rail legs, door mirror stays, bumpers, spoilers and wheel covers, automobile interior parts such as cup holders, console boxes, accelerator pedals, clutch pedals, shift lever pedestals and shift lever knobs.

Further, the polyamide resin and the polyamide resin composition of the present invention may also be used in various applications, e.g., fishing-related materials such as fishing lines and fishing nets; and electric and electronic related parts, domestic and office electric equipment parts, computer-related parts, facsimile and copier-related parts and mechanical parts such as typically switches, micro slide switches, DIP switches, switch housings, lamp sockets, binding bands, connectors, connector housings, connector shells, IC sockets, coil bobbins, bobbin covers, relays, relay boxes, capacitor cases, motor interior parts, small size motor cases, gears and cams, dancing pulleys, spacers, insulators, casters, terminal boards, electric tool housings, starter insulating portions, fuse boxes, terminal housings, bearing retainers, speaker diaphragms, heat-resisting containers, electronic oven parts, rice boiler parts and printer ribbon guides.

Next, the hinged molded product according to the eighth aspect of the present invention is explained. The hinged molded product according to the eighth aspect of the present invention contains the polyamide resin constituted of an adipic acid unit and a pentamethylenediamine unit, and may comprise the polyamide resin solely.

The content of the adipic acid unit in the dicarboxylic acid constitutional unit forming the polyamide resin is usually not less than 90% by weight, preferably not less than 95% by weight, and the dicarboxylic acid constitutional unit may comprise the adipic acid unit solely. The content of the pentamethylenediamine unit in the diamine constitutional unit forming the polyamide resin is usually not less than 90% by weight, preferably not less than 95% by weight, and the diamine constitutional unit may comprise the pentamethylenediamine unit solely.

The polyamide resin used in the eighth aspect of the present invention may contain comonomer components other than the essential pentamethylenediamine and adipic acid constitutional units in an amount of usually less than 10% by weight, and preferably less than 5% by weight based on the weight of the whole constitutional units, unless the addition thereof adversely affects the aimed effects of the present invention. As the comonomer components, there may be used such comonomer components as explained with respect to the polyamide resins according to the first and second aspect of the present invention, dicarboxylic acids as a comonomer, and diamines as a comonomer (1,6-diaminohexane is also usable).

The polymerization degree of the polyamide resin used in the eighth aspect of the present invention is not particularly limited, and may be substantially identical to those of the polyamide resins according to the first and second aspects of the present invention.

The polyamide resin used in the eighth aspect of the present invention usually has two melting points (Tm), i.e., about 255° C. and about 232° C. Meanwhile, the method of measuring the melting points is substantially identical to the method used for measuring the melting point of the polyamide resins according to the first and second aspects of the present invention.

The production method, heat-polycondensation, solid phase polycondensation and polymerization method of the polyamide resin used in the eighth aspect of the present invention are substantially identical to those described with respect to the polyamide resins according to the first and second aspects of the present invention.

In the polyamide resin used in the eighth aspect of the present invention which is produced by the above method, pentamethylenediamine as a raw component thereof is preferably produced from lysine using a lysine decarboxylase, cells capable of producing the lysine decarboxylase or a treated product of the cells. By using such a pentamethylenediamine as produced from lysine, the biomass ratio of the polyamide resin (ratio of a biomass-derived raw material to whole raw materials used in the polyamide resin) can be enhanced. The biomass ratio of the polyamide resin (ratio of a biomass-derived raw material to whole raw materials used in the polyamide resin) is preferably not less than 25%. When the biomass ratio is less than 25%, it may be difficult to attain the effect of suppressing generation of carbon dioxide causing the global warming problem.

The method of producing the above pentamethylenediamine is substantially identical to the production method described with respect to the polyamide resins according to the first and second aspects of the present invention.

The polyamide resin used in the eighth aspect of the present invention may be blended with other components at any optional stage from production (polycondensation) of the polyamide resin to molding thereof, unless the addition thereof adversely affects the aimed effects of the present invention. Examples of the other components blended in the polyamide resin may include those described with respect to the polyamide resins according to the first and second aspects of the present invention, namely, nucleating agents, antioxidants and/or heat stabilizers, weather-resisting agents, mold release agents and/or lubricants, pigments, dyes, plasticizers, antistatic agents, flame retardants and other polymers. Among these components, when the polyamide resin is used for injection-molding and non-reinforcing purposes for hinged molded products, binding bands, etc., the nucleating agent or mold release agent is preferably dry-blended in the polyamide resin in order to enhance a moldability thereof, unless the addition thereof adversely affects the aimed effects of the present invention.

The hinged molded product according to the eighth aspect of the present invention may be obtained by forming the polyamide resin of the present invention into a desired shape by an optional molding method. Examples of the molding method may include an injection-molding method, a film-forming method, a melt-sinning method, a blow-molding method and a vacuum forming method. Among these molding methods, especially preferred is the injection-molding method.

Specific examples of the hinged molded product and the thickness of the hinged portion thereof are substantially identical to those described with respect to the hinged molded product according to the fifth aspect of the present invention.

EXAMPLES

The present invention is described in more detail below by the following examples, but these examples are only illustrative and not intended to limit the scope of the present invention. Meanwhile, among the following Examples and Reference Examples, Examples 1 to 8 and Reference Examples 1 to 5 are concerned with the first to seventh aspects of the present invention and Example 9 and Reference Example 6 are concerned with the eighth aspect of the present invention. Various properties described in the present invention were measured by the following methods.

The present invention is described in more detail below by the following examples, but these examples are only illustrative and not intended to limit the scope of the present invention. The methods for evaluating various properties of the polyamide resin, the polyamide resin composition, the molded products produced therefrom, and the hinged molded product are explained below.

(1) Relative Viscosity ($\eta r$):

A 98% sulfuric acid solution of the polyamide resin (concentration: 0.01 g/mL) was prepared, and a relative viscosity thereof was measured at 25° C. using an Ostwald type viscometer.

(2) DSC (Differential Scanning Calorimetry):

The DSC measurement was conducted using "Robot DSC" manufactured by Seiko Denshi Kogyo Co., Ltd. First, about 5 mg of the polyamide resin was charged into a sampling pan, and heated to 290° C. under a nitrogen atmosphere and held at 290° C. for 3 min to completely melt the resin. Thereafter, the molten polyamide resin was cooled to 30° C. at a temperature drop rate of 20° C./min to measure an exothermic peak temperature observed during the temperature drop. The thus observed exothermic peak temperature was determined as a temperature-drop crystallization temperature (T(° C.)). Successively, the polyamide resin was held at 30° C. for 3 min, and then heated again from 30° C. to 290° C. at a temperature rise rate of 20° C./min to measure an endothermic peak thereof and determine an endothermic peak area therefrom. The temperature of the thus observed endothermic peak was determined as a melting point (Tm) of the polyamide resin. When a plurality of endothermic peaks were detected, the temperatures thereof were determined as a plurality of melting points of the polyamide resin.

(3) Retention Heat Stability:

7 g of the polyamide resin as a sample was placed in a 18 cc test tube, and the test tube filled with the sample was hermetically sealed under a nitrogen atmosphere and immersed in an oil bath maintained at a temperature higher by 30° C. than the melting point of the polyamide resin (melting point+30° C.). After the elapse of 9 hr, the sample was recovered to measure a relative viscosity thereof. A viscosity retention rate of the polyamide resin was calculated from the relative viscosity values thereof measured before and after the retention test.

(4) Vibration-Welding Test:

(4-1) Pressure Test for Hollow Product:

<Primary Molding of Parts of Hollow Product>

Figure 3:
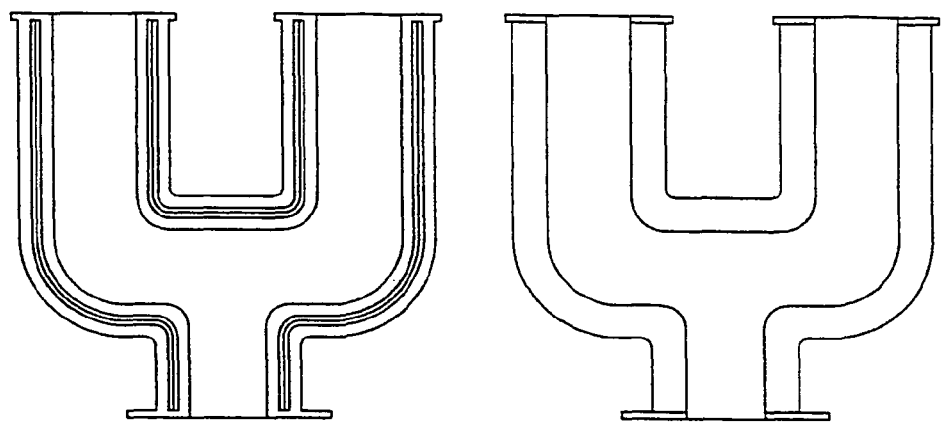

A glass fiber-reinforced polyamide resin composition was formed into a pair of parts of a hollow product each having a thickness of 2 mm and a welding surface width of 4 mm as primary molded products as shown in FIGS. 3(a) and 3(b). The primary molding was performed at a resin temperature of 270° C. and a mold temperature of 80° C. using an injection molding machine "IS 350 Model" manufactured by Toshiba Kikai Co., Ltd.

<Vibration Welding of Parts of Hollow Product>

Figure 4:
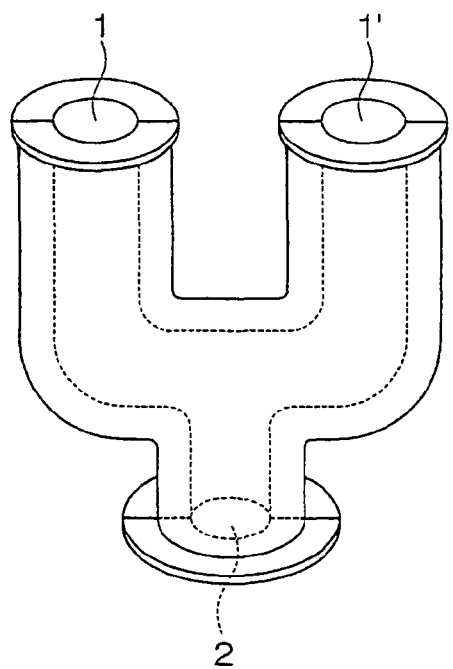
FIG. 4 is a perspective view showing the hollow part used in a vibration welding test in Examples according to the present invention.

Using a vibration welding machine "VIBRATION WELDER Model 2800" manufactured by Emerson Japan, Ltd., the above pair of parts of the hollow product were bonded together by vibration welding. The vibration welding was conducted under the conditions including a welding pressure as shown in Table 1, a vibration frequency of 240 Hz, a vibration amplitude of 1.5 mm, a welding margin of 1.5 mm, a retention pressure substantially identical to the welding pressure immediately before stopping the vibration, and a retention time of 5.0 sec, thereby obtaining a vibration-welded molded product (hollow product) as shown in FIG. 4. Upon the above vibration welding, the dimension of the welding margin of each part of the hollow product was controlled using a non-contact welding dimension controller (WDC) "CX132 Model" manufactured by Emerson Japan, Ltd.

<Pressure Test for Hollow Product>

The thus obtained hollow product was subjected to a pressure test. Using a pressure tester manufactured by Toyo. Seiki Seisakusho Co., Ltd., two upper openings (1) and (1') (opening diameter: 32 mmφ) of the hollow product were closed, and a hydraulic pressure was applied to an inside of the hollow product through a lower opening (2) (opening diameter: 32 mmφ) at a pressure gradation rate of 980 kPa/min to measure the pressure upon breaking of the vibration-welded molded product. The test was repeated 3 times every welding pressure, and an average of the measured values was calculated to determine a pressure-resisting strength of the hollow product.

(4-2) Vibration-Welding Strength Test for Rectangular Test Piece:

<Primary Molding of Rectangular Test Piece>

A glass fiber-reinforced polyamide resin composition was molded to form two primary molded products of a rectangular parallelopiped shape each having a bottom surface of 25 mm×4 mm and a height of 60 mm. The primary molding was conducted at a resin temperature of 270° C. and a mold temperature of 80° C. using an injection molding machine "J75-ED Model" manufactured by Japan Steel Works, LTD.

<Vibration Welding of Rectangular Test Piece>

Using a vibration welding machine "VIBRATION WELDER Model 2800" manufactured by Emerson Japan, Ltd., the above two primary molded products were bonded together at bottom surfaces thereof by vibration welding. The vibration welding was conducted under the conditions including a welding pressure as shown in Table 1, a vibration frequency of 240 Hz, a vibration amplitude of 1.5 mm, a welding margin of 1.5 mm, a retention pressure substantially identical to the welding pressure immediately before stopping the vibration, and a retention time of 5.0 sec, thereby obtaining a vibration-welded molded product constituted from the above two primary molded products welded together at the bottom surfaces thereof. Upon the above vibration welding, the dimension of the welding margin of the vibration-welded molded product was controlled using a non-contact welding dimension controller (WDC) "CX132 Model" manufactured by Emerson Japan, Ltd.

<Vibration Welding Strength Test for Rectangular Test Piece>

The thus obtained vibration-welded molded product was subjected to a vibration welding strength test. Using "TENSILON UTM-III-2500" manufactured by A & D Corp., the vibration-welded molded product was subjected to a tensile test at a distance between chucks of 60 mm and a pulling velocity of 5 mm/min to measure a strength thereof upon breaking. The six molded products were tested every welding pressure, and an average of the measured values was calculated to determine a vibration welding strength of the molded product.

(5) Evaluation of Mechanical Properties (Tensile Test, Bending Test and Notched Charpy Impact Test)

The glass fiber-reinforced polyamide resin composition and the non-reinforced polyamide resin composition were respectively molded into ISO test pieces according to ISO Standard. The molding was conducted using an injection molding machine "J75EII Model" manufactured by Japan Steel Works, LTD., at a resin temperature of 270° C. and a mold temperature of 80° C. for the glass fiber-reinforced polyamide resin composition or at a resin temperature of 265° C. and a mold temperature of 80° C. for the non-reinforced polyamide resin composition. The thus molded ISO test pieces were subjected to a tensile test, a bending test and a notched Charpy impact test according to respective ISO Standards.

Figure 5:
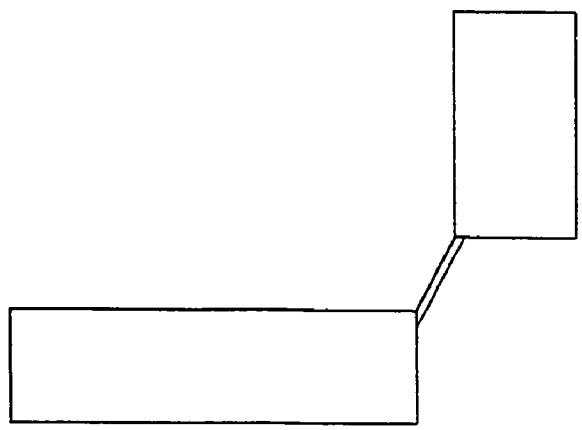
FIGS. 5(a) and 5(b) are a side view and a top view, respectively, showing a hinged molded product used in a low-temperature hinge property test in Examples according to the present invention.
Figure 5:
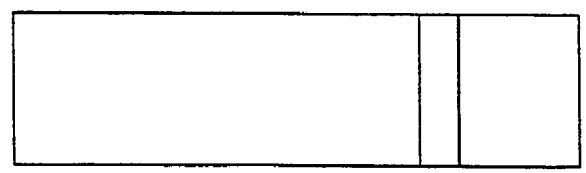
Figure 6:
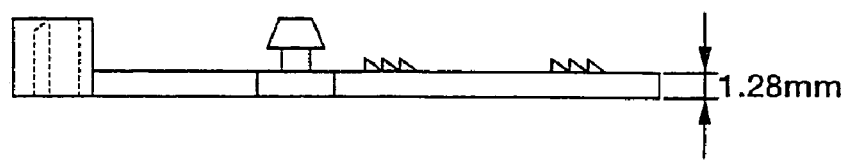
FIGS. 6(a) and 6(b) are a side view and a top view, respectively, showing a binding band used in a low-temperature band breaking test in Examples according to the present invention.
Figure 6:
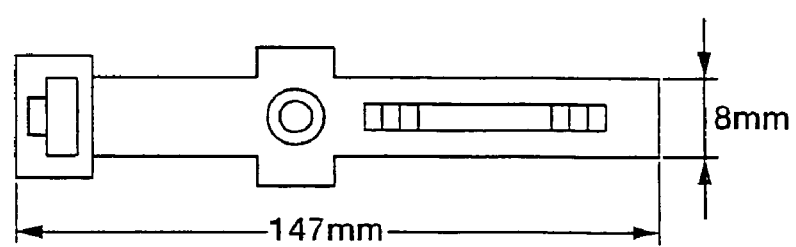

(6) Low-Temperature Hinge Property:

The non-reinforced polyamide resin composition was molded into a hinged molded product as shown in FIG. 5 and a binding band as shown in FIG. 6. The molding of the hinged molded product was conducted using an injection molding machine "PS40 Model" manufactured by Nissei Plastic Industrial Co., Ltd., at a resin temperature of 265° C. and a mold temperature of 80° C. The molding of the binding band was conducted using an injection molding machine "SE50D Model" manufactured by Sumitomo Heavy Industries, Ltd., at a resin temperature of 265° C. and a mold temperature of 80° C. The hinged portion of these molded products had a length of 2 mm, a width of 40 mm and a thickness of 0.4 mm.

Figure 7:
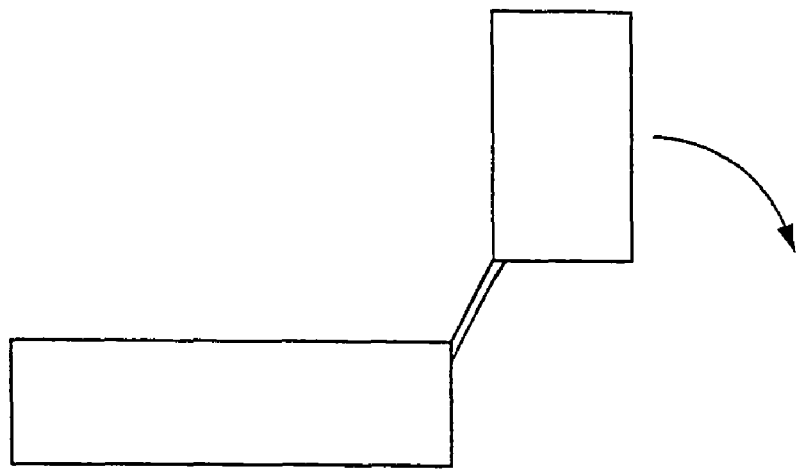
FIG. 7 is an explanatory view for a low-temperature hinge property test conducted in Examples according to the present invention.

The hinged molded product was cooled in a constant-temperature oven maintained at a temperature shown in Table 2 for 2 hr. Meanwhile, as the constant-temperature oven, there was used a large-size chamber capable of allowing a measuring person to enter therein for conducting the test. After cooling the hinged molded product for 2 hr, the measuring person entered into the constant-temperature oven and was standing-by for 10 min to completely eliminate adverse influences of temperature change due to the entrance of the measuring person. Thereafter, the test was conducted by bending the hinged portion from 90° (perpendicularly bent state) to 180° (flat state relative to a floor) as shown in FIG. 7. More specifically, while holding the molded product at its horizontal surface portion with one hand, the vertical surface portion thereof was rapidly bent with the other hand. The twenty hinged molded products were tested every measuring temperature. The number of the hinged molded products whose hinged products were free from breakage was counted as a measured value of the test.

Figure 8:
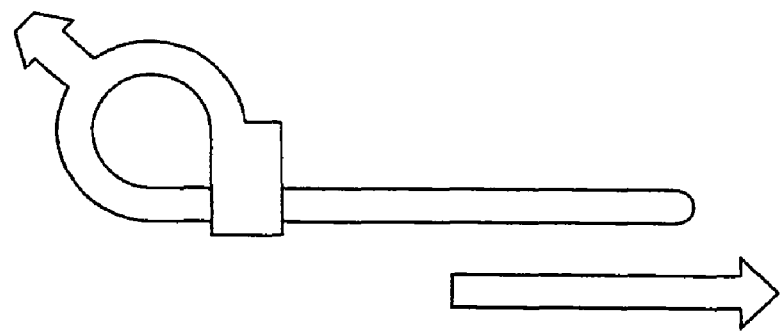
FIG. 8 is an explanatory view for a low-temperature band breaking test conducted in Examples according to the present invention.

(7) Low-Temperature Band Breaking Property:

The binding band was cooled in the constant-temperature oven at a temperature as shown in Table 2. Meanwhile, as the constant-temperature oven, there was used a large-size chamber capable of allowing a measuring person to enter therein for conducting the test. After cooling the binding band for 2 hr, the measuring person entered into the constant-temperature oven and was standing-by for 10 min to completely eliminate adverse influences of temperature change due to the entrance of the measuring person. Thereafter, the test was conducted by inserting one end of the band into an opening provided at the other end of the band as shown in FIG. 8 and then strongly pulling the one end of the band while holding the other end thereof with one hand. The twenty binding bands were tested every measuring temperature. The number of the binding bands which were free from breakage was counted as a measured value of the test.

(8) Transparency of Monofilament:

A 40 mmφ single-screw extruder manufactured by UNI-PLAS CORPORATION, and equipped at its tip end with a gear pump and a nozzle with 18 holes each having a diameter of 0.6 mm was used as an extruder for spinning. The polyamide resin was melted at a temperature higher by 20° C. than the melting point of the polyamide resin (melting point+20° C.), and melt-spun using the above extruder, passed through a cooling water vessel at 20° C. to cool and solidify the spun resin, stretched at 98° C. in a wet heat condition, subjected to second-stage stretching in a hot-air stretching vessel at 172° C. and then thermally fixed in the hot-air stretching vessel at 168° C., thereby obtaining a monofilament having a diameter of 0.079 mm. The thus obtained monofilament was visually observed to evaluate a transparency thereof.

In the following Examples and Reference Examples, "AH salt" produced by Rhodia Ltd., was used as an equimolar salt of hexamethylenediamine and adipic acid. Whereas, an equimolar salt of pentamethylenediamine and adipic acid was produced by the method described in Examples 1 to 3 of Japanese Patent Application Laid-open (KOKAI) No. 2005-6650.

Example 1

Polyamide Resin Composition and Vibration Welded Molded Product 25 kg of water was added to 25 kg of a mixture containing the equimolar salt of pentamethylenediamine and adipic acid and the equimolar salt of hexamethylenediamine and adipic acid (as to the weight ratio therebetween, refer to Table 1), and then 1.25 g of phosphorous acid was added thereto to completely dissolve the mixture under a nitrogen atmosphere, thereby obtaining a raw material aqueous solution. The thus obtained raw material aqueous solution was transported into an autoclave previously purged with nitrogen using a plunger pump. By adjusting a jacket temperature and a pressure in the autoclave to 280° C. and 1.47 MPa, respectively, the contents of the autoclave were heated to 270° C. Next, the inside pressure of the autoclave was gradually released and further reduced to terminate the reaction at the time at which the agitation power reached a predetermined value. After completion of the reaction, the inside pressure of the autoclave was restored by supplying nitrogen thereinto, and the contents of the autoclave were introduced into a cooling water vessel in the form of a strand, and then pelletized using a rotary cutter. The resultant pellets were dried at 120° C. and 1 torr (0.13 kPa) until the water content thereof reached 0.1% or lower, thereby obtaining a polyamide resin. The thus obtained polyamide resin was subjected to evaluation of various properties thereof.

100 parts by weight of the obtained polyamide resin was blended with 43 parts by weight of a glass fiber "T249H" produced by Nippon Electric Glass Co., Ltd., thereby obtaining a glass fiber-reinforced polyamide resin composition. The blending was conducted using a twin-screw kneader "TEM-35B Model" manufactured by Toshiba Machine Co., Ltd. The glass fiber was side-fed in order to avoid a breakage thereof, and the melt-kneading temperature was adjusted to 270° C. The thus obtained polyamide resin composition was subjected to vibration-welding test and evaluation of mechanical properties thereof. The results are shown in Table 1.

Reference Example 1

The same procedure as defined in Example 1 was Conducted except that the composition of monomers charged in the raw salts was changed as shown in Table 1, thereby obtaining a polyamide resin. The thus obtained polyamide resin was blended with a glass fiber by the same method as defined in Example 1, thereby obtaining a glass fiber-reinforced polyamide resin composition. The thus obtained polyamide resin composition was subjected to vibration-welding test and evaluation of mechanical properties thereof. The results are shown in Table 1.

Example 2

Polyamide Resin Composition, Hinged Molded Product and Binding Band 100 parts by weight of the polyamide resin obtained in Example 1 was blended with 0.02 part by weight of talc as a nucleating agent having an average particle size of 3.0 μm and then dry-blended, thereby obtaining a non-reinforced polyamide resin composition. The thus obtained polyamide resin composition was subjected to evaluation of a low-temperature hinge property, a low-temperature band breaking property and mechanical properties thereof. The results are shown in Table 2.

Reference Example 2

The same procedure as defined in Example 1 was conducted except that the composition of monomers charged in the raw material aqueous solution was changed as shown in Table 1, thereby obtaining a polyamide resin. The thus obtained polyamide resin was blended with talc by the same method as defined in Example 2 and then dry-blended with each other, thereby obtaining a non-reinforced polyamide resin composition. The thus obtained polyamide resin composition was subjected to evaluation of a low-temperature hinge property, a low-temperature band breaking property and mechanical properties thereof. The results are shown in Table 2.

Reference Example 3

25 kg of caprolactam produced by Mitsubishi Chemical Corporation, 0.75 kg of water and 1.74 g of disodium hydrogen phosphite pentahydrate were charged into a container, and after the container was purged with nitrogen, the contents of the container were dissolved at 100° C. The thus obtained raw material aqueous solution was transported into an autoclave. The heating of the solution was initiated by adjusting a jacket temperature to 280° C. Next, after heating the contents of the autoclave to 270° C., the inside pressure of the autoclave was gradually released and further reduced to terminate the polycondensation reaction at the time at which the agitation power reached a predetermined value. After completion of the reaction, the inside pressure of the autoclave was restored by supplying nitrogen thereinto, and the contents of the autoclave were introduced into a cooling water vessel in the form of a strand, and then pelletized using a rotary cutter. The resultant pellets were treated with a boiled water in an amount of 1.5 times the amount of the pellets to extract and remove unreacted monomers and oligomers therefrom. The pellets from which the unreacted compounds were removed, were dried at 120° C. and 1 torr (0.13 kPa) until the water content thereof reached 0.1% or lower, thereby obtaining a polyamide resin. The thus obtained polyamide resin was subjected to evaluation of various properties thereof.

The obtained polyamide resin was blended with talc by the same method as defined in Example 2 and then dry-blended with each other, thereby obtaining a non-reinforced polyamide resin composition. The thus obtained polyamide resin composition was subjected to evaluation of a low-temperature hinge property, a low-temperature band breaking property and mechanical properties thereof. The results are shown in Table 2.

Examples 3 to 8

Polyamide Resin and Filament

The same procedure as defined in Example 1 was conducted except that the composition of monomers charged in the raw material aqueous solution was changed as shown in Tables 3 and 4, thereby obtaining a polyamide resin. The thus obtained polyamide resin was subjected to evaluation of various properties thereof. Further, the obtained polyamide resin was formed into a monofilament by the method described in the above item "evaluation of transparency", to evaluate a transparency thereof. The results are shown in Tables 3 and 4.

Reference Example 4

The same procedure as defined in Example 1 was conducted except that the composition of monomers charged in the raw material aqueous solution was changed as shown in Table 5, thereby obtaining a polyamide resin. The thus obtained polyamide resin was subjected to evaluation of various properties thereof. Further, the obtained polyamide resin was formed into a monofilament by the method described in the above item "evaluation of transparency", to evaluate a transparency thereof. The results are shown in Table 5.

Reference Example 5

The same procedure as defined in Example 1 was conducted except that the composition of monomers charged in the raw material aqueous solution was changed as shown in Table 5, thereby obtaining a polyamide resin. The thus obtained polyamide resin was subjected to evaluation of various properties thereof. Further, the obtained polyamide resin was formed into a monofilament by the method described in the above item "evaluation of transparency", to evaluate a transparency thereof. The results are shown in Table 5.

TABLE 1

| | Unit | Example 1 | Reference Example 1 |
|---|---|---|---|
| Composition of monomers charged | | | |
| Salt of pentamethylenediamine and adipic acid | wt % | 80 | 100 |
| Salt of hexamethylenediamine and adipic acid | wt % | 20 | 0 |
| ε-Caprolactum | wt % | 0 | 0 |
| Properties of polyamide resin | | | |
| Polyamide resin | — | 56/66 nylon | 56 nylon |
| Relative viscosity [ηr] | — | 3.00 | 3.00 |
| Melting point (Tm) | ° C. | 245; 233 | 255; 232 |
| Ratio of endothermic peak area as measured at 240° C. or higher | % | 28 | 62 |
| Relative viscosity after retention test | — | 2.65 | 2.18 |
| Relative viscosity retention rate after retention test | % | 88.3 | 72.7 |
| Blending ratio of resin composition | | | |
| Glass fiber | wt part | 43 | 43 |
| Pressure-resisting strength Welding pressure | | | |
| 0.98 MPa | kPa | 1270 | 1210 |
| 1.47 MPa | kPa | 1170 | 1140 |
| 2.45 MPa | kPa | 1130 | 1060 |
| Vibration-welding strength Welding pressure | | | |
| 1.52 MPa | MPa | 66.7 | 65.3 |
| 2.55 MPa | MPa | 68.5 | 59.7 |
| 3.82 MPa | MPa | 60.0 | 57.1 |
| Mechanical properties | | | |
| Tensile strength | MPa | 190 | 189 |
| Tensile elongation | % | 4.1 | 3.8 |
| Bending strength | MPa | 251 | 253 |
| Bending modulus | MPa | 8490 | 8610 |
| Notched Charpy impact strength | kJ/m$^2$ | 7.7 | 7.3 |
| Biomass ratio of polyamide resin[1] | % | 33 | 41 |

Note
[1]Ratio of biomass-derived raw material to whole raw materials used in the polyamide resin

TABLE 2

|  | Unit | Example 2 | Reference Examples 2 | Reference Examples 3 |
| --- | --- | --- | --- | --- |
| Composition of monomers charged | | | | |
| Salt of pentamethylenediamine and adipic acid | wt % | 80 | 100 | 0 |
| Salt of hexamethylenediamine and adipic acid | wt % | 20 | 0 | 0 |
| ε-Caprolactum | wt % | 0 | 0 | 100 |
| Properties of polyamide resin | | | | |
| Polyamide resin | — | 56/66 nylon | 56 nylon | 6 nylon |
| Relative viscosity [ηr] | — | 3.00 | 3.00 | 3.00 |
| Melting point (Tm) | °C. | 245; 233 | 255; 232 | 224 |
| Ratio of endothermic peak area as measured at 240° C. or higher | % | 28 | 62 | 0 |
| Relative viscosity after retention test | — | 2.65 | 2.18 | — |
| Relative viscosity retention rate after retention test | % | 88.3 | 72.7 | — |
| Blending ratio of resin composition | | | | |
| Talc | wt part | 0.02 | 0.02 | 0.02 |
| Low-temperature hinge property (number of specimens free from breakage after testing total 20 specimens) | | | | |
| Temperature of constant-temperature oven | | | | |
| −20° C. | — | — | 19 | 20 | 6 |
| −30° C. | — | — | 18 | 20 | 1 |
| −40° C. | — | — | 17 | 17 | 0 |
| Low-temperature band breaking property (number of specimens free from breakage after testing total 20 specimens) | | | | |
| Temperature of constant-temperature oven | | | | |
| −10° C. | — | — | 17 | 9 | 19 |
| −15° C. | — | — | 13 | 1 | 19 |
| −20° C. | — | — | 5 | 0 | 13 |
| Mechanical properties | | | | |
| Tensile strength | MPa | 86 | 88 | 82 |
| Tensile elongation | % | 26 | 25 | 32 |
| Bending strength | MPa | 107 | 111 | 98 |
| Bending modulus | MPa | 2860 | 2850 | 2710 |
| Notched Charpy impact strength | kJ/m² | 7.9 | 6.9 | 8.7 |
| Biomass ratio of polyamide resin | % | 33 | 41 | 0 |

Note
[1] Ratio of biomass-derived raw material to whole raw materials used in the polyamide resin

TABLE 3

|  | | Examples | | |
| --- | --- | --- | --- | --- |
|  | Unit | 3 | 4 | 5 |
| Composition of monomers charged | | | | |
| Salt of pentamethylene-diamine and adipic acid | wt % | 90 | 80 | 60 |
| Salt of hexamethylenediamine and adipic acid | wt % | 10 | 20 | 40 |
| ε-Caprolactum | wt % | 0 | 0 | 0 |

TABLE 3-continued

|  | | Examples | | |
| --- | --- | --- | --- | --- |
|  | Unit | 3 | 4 | 5 |
| Properties of polyamide resin | | | | |
| Polyamide resin | — | 56/66 nylon | 56/66 nylon | 56/66 nylon |
| Relative viscosity [ηr] | — | 3.43 | 3.50 | 3.42 |
| Melting point (Tm) | °C. | 250; 231 | 247; 231 | 225; 184 |
| Temperature-drop crystallization temperature | °C. | 190 | 183 | 175 |
| Moldability | | | | |
| Molding temperature | °C. | 270 | 267 | 245 |
| Transparency of filament | — | Transparent | Transparent | Transparent |

TABLE 4

|  | | Examples | | |
| --- | --- | --- | --- | --- |
|  | Unit | 6 | 7 | 8 |
| Composition of monomers charged | | | | |
| Salt of pentamethylene-diamine and adipic acid | wt % | 40 | 20 | 15 |
| Salt of hexamethylene-diamine and adipic acid | wt % | 60 | 80 | 85 |
| ε-Caprolactum | wt % | 0 | 0 | 0 |
| Properties of polyamide resin | | | | |
| Polyamide resin | — | 56/66 nylon | 56/66 nylon | 56/66 nylon |
| Relative viscosity [ηr] | — | 3.48 | 3.52 | 3.60 |
| Melting point (Tm) | °C. | 229; 207 | 245 | 250 |
| Temperature-drop crystallization temperature | °C. | 181 | 195 | 197 |
| Moldability | | | | |
| Molding temperature | °C. | 249 | 265 | 270 |
| Transparency of filament | — | Transparent | Transparent | Transparent |

TABLE 5

|  | | Reference Examples | |
| --- | --- | --- | --- |
|  | Unit | 4 | 5 |
| Composition of monomers charged | | | |
| Salt of pentamethylenediamine and adipic acid | wt % | 100 | 0 |
| Salt of hexamethylenediamine and adipic acid | wt % | 0 | 100 |
| ε-Caprolactum | wt % | 0 | 0 |
| Properties of polyamide resin | | | |
| Polyamide resin | — | 56 nylon | 66 nylon |
| Relative viscosity [ηr] | — | 3.72 | 4.06 |
| Melting point (Tm) | °C. | 256; 233 | 266 |
| Temperature-drop crystallization temperature | °C. | 200 | 211 |

TABLE 5-continued

|  | Unit | Reference Examples | |
|---|---|---|---|
|  |  | 4 | 5 |
| Moldability | | | |
| Molding temperature | °C. | 276 | 286 |
| Transparency of filament | — | Opaque | Opaque |

Example 9

25 kg of water was added to 25 kg of an equimolar salt of pentamethylenediamine and adipic acid, and then 1.25 g of phosphorous acid was added thereto to completely dissolve the mixture under a nitrogen atmosphere, thereby obtaining a raw material aqueous solution. The thus obtained raw material aqueous solution was transported into an autoclave previously purged with nitrogen using a plunger pump. By adjusting a jacket temperature and a pressure in the autoclave to 280° C. and 1.47 MPa, respectively, the contents of the autoclave were heated to 270° C. Next, the inside pressure of the autoclave was gradually released and further reduced to terminate the reaction at the time at which the agitation power reached a predetermined value. After completion of the reaction, the inside pressure of the autoclave was restored by supplying nitrogen thereinto, and the contents of the autoclave were introduced into a cooling water vessel in the form of a strand, and then pelletized using a rotary cutter. The resultant pellets were dried at 120° C. and 1 torr (0.13 kPa) until the water content thereof reached 0.1% or lower, thereby obtaining a polyamide resin. The thus obtained polyamide resin was subjected to evaluation of various properties thereof. The results are shown in Table 6.

100 parts by weight of the obtained polyamide resin was blended with 0.02 part by weight of talc as a nucleating agent having an average particle size of 3.0 μm and then dry-blended with each other, thereby obtaining a non-reinforced polyamide resin composition. The thus obtained polyamide resin composition was subjected to evaluation of a low-temperature hinge property and mechanical properties thereof. The results are shown in Table 6.

Reference Example 6

25 kg of caprolactam produced by Mitsubishi Chemical Corporation, 0.75 kg of water and 1.74 g of disodium hydrogen phosphite pentahydrate were charged into a container, and after the container was purged with nitrogen, the contents of the container were dissolved at 100° C. The thus obtained raw material aqueous solution was transported into an autoclave. The heating of the solution was initiated by adjusting a jacket temperature to 280° C. After heating the contents of the autoclave to 270° C., the inside pressure of the autoclave was gradually released and further reduced to terminate the polycondensation reaction at the time at which the agitation power reached a predetermined value. After completion of the reaction, the inside pressure of the autoclave was restored by supplying nitrogen thereinto, and the contents of the autoclave were introduced into a cooling water vessel in the form of a strand, and then pelletized using a rotary cutter. The resultant pellets were treated with a boiled water in an amount of 1.5 times the amount of the pellets to extract and remove unreacted monomers and oligomers therefrom. The pellets from which the unreacted compounds were removed, were dried at 120° C. and 1 torr (0.13 kPa) until the water content thereof reached 0.1% or lower, thereby obtaining a polyamide resin. The thus obtained polyamide resin was subjected to evaluation of various properties thereof.

The obtained polyamide resin was blended with talc by the same method as defined in Example 9 and then dry-blended together, thereby obtaining a non-reinforced polyamide resin composition. The thus obtained polyamide resin composition was subjected to evaluation of a low-temperature hinge property and mechanical properties thereof. The results are shown in Table 6.

TABLE 6

|  | Unit | Example 9 | Reference Example 6 |
|---|---|---|---|
| Composition of monomers charged | | | |
| Salt of pentamethylenediamine and adipic acid | wt % | 100 | 0 |
| ε-Caprolactum | wt % | 0 | 100 |
| Properties of polyamide resin | | | |
| Polyamide resin | — | 56 nylon | 6 nylon |
| Relative viscosity | — | 3.00 | 3.00 |
| Melting point (Tm) | °C. | 255; 232 | 224 |
| Blending ratio of resin composition | | | |
| Talc | wt part | 0.02 | 0.02 |
| Low-temperature hinge property (number of specimens free from breakage after testing total 20 specimens) | | | |
| Temperature of constant-temperature oven | | | |
| −20° C. | — | 20 | 6 |
| −30° C. | — | 20 | 1 |
| −40° C. | — | 17 | 0 |
| Mechanical properties | | | |
| Tensile yield stress | MPa | 88 | 82 |
| Tensile break strain | % | 25 | 32 |
| Bending strength | MPa | 111 | 98 |
| Bending modulus | MPa | 2850 | 2710 |
| Notched Charpy impact strength | $kJ/m^2$ | 6.9 | 8.7 |
| Biomass ratio of polyamide resin[1] | % | 41 | 0 |

Note
[1] Ratio of biomass-derived raw material to whole raw materials used in the polyamide resin Although the present invention is described above with respect to embodiments which are considered to be most practical and preferable at the present time, the present invention is not limited to these embodiments, and various changes and modifications will be appropriately made within the scope of claims and a whole of a specification of this application unless departing from the subject matter and concept of the present invention, and it should be construed that the changes and modifications are involved in technical range of the present invention. Meanwhile, the present patent application is based on Japanese Patent Application No. 2004-152059 filed on May 21, 2004, Japanese Patent Application No. 2005-144478 filed on May 17, 2005 and Japanese Patent Application No. 2005-145847 filed on May 18, 2005 whole contents of which are incorporated herein by reference.

The invention claimed is:

1. A hinged molded product or binding band which has a hinged portion having a thickness of 0.2 to 0.8 mm and comprises a polyamide resin comprising a dicarboxylic acid constitutional unit comprising an adipic acid unit and a diamine constitutional unit comprising a pentamethylenediamine unit and a hexamethylenediamine unit, a weight ratio of the pentamethylenediamine unit to the hexamethylenediamine unit being in a range of 95:5 to 60:40.

2. A hinged molded product or binding band according to claim 1, further comprising an inorganic filler in an amount of 0.01 to 150 parts by weight on the basis of 100 parts by weight of the polyamide resin, which inorganic filler is blended into the polyamide resin to form a polyamide resin composition.

3. A process for producing a vibration-welded hinged molded product or binding band which has a hinged portion comprising:
    producing a polyamide resin comprising a dicarboxylic acid constitutional unit comprising an adipic acid unit and a diamine constitutional unit comprising a pentamethylenediamine unit and a hexamethylenediamine unit, a weight ratio of the pentamethylenediamine unit to the hexamethylenediamine unit being in a range of 95:5 to 60:40,
    molding the polyamide resin into a molded parts as primary molded products and
    bonding a plurality of the molded parts together by vibration welding under a frequency of vibration of 100 to 300 Hz, an amplitude of 0.5 to 2.0 mm and welding pressure of 0.5 to 10 MPa.

4. The process according to claim 3 further comprising blending an inorganic filler into the polyamide resin in a content of 0.01 to 150 parts by weight on the basis of 100 parts by weight of the polyamide resin to obtain a polyamide resin composition.

5. A vibration-welded hinged molded product or binding band which has a hinged portion produced by the process according to claim 3.

* * * * *